United States Patent [19]
Auguste et al.

[11] Patent Number: 5,985,807
[45] Date of Patent: Nov. 16, 1999

[54] USE OF AN ORGANOPOLYSILOXANE OF ELASTOMERIC NATURE IN COMBINATION WITH AN ORGANIC PHASE IN A PRODUCT FOR REMOVING MAKE-UP FROM THE NAILS

[75] Inventors: Frédéric Auguste, Chevilly-Larue; Isabelle Bara, Paris, both of France

[73] Assignee: L'Oreal, France

[21] Appl. No.: 08/944,419

[22] Filed: Oct. 6, 1997

[30] Foreign Application Priority Data

Oct. 6, 1996 [FR] France ................................. 96 12197

[51] Int. Cl.$^6$ ................................. C11D 7/22; C11D 7/50
[52] U.S. Cl. ........................... 510/118; 510/466; 134/38; 134/39; 424/61
[58] Field of Search ..................... 510/118, 466; 134/38, 39; 424/61

[56] References Cited

U.S. PATENT DOCUMENTS

| | | | |
|---|---|---|---|
| 5,091,105 | 2/1992 | Madore et al. | 252/174 |
| 5,266,321 | 11/1993 | Shukuzaki et al. | 424/401 |
| 5,342,536 | 8/1994 | Miner et al. | 252/162 |
| 5,486,305 | 1/1996 | Faryniarz et al. | 252/162 |
| 5,486,306 | 1/1996 | L'Hostis et al. | 252/174.15 |
| 5,520,908 | 5/1996 | Lundmark | 424/70.1 |
| 5,543,085 | 8/1996 | Miner | 510/118 |

OTHER PUBLICATIONS

Miwa Yasuyuki et al., "Manicure Removing Agent," Patent Abstracts of Japan, Publication No. 63–159307, Publication Date Jul. 2, 1998.

*Primary Examiner*—Yogendra Gupta
*Assistant Examiner*—Gregory R. Del Cotto
*Attorney, Agent, or Firm*—Finnegan, Henderson, Farabow, Garrett & Dunner, L.L.P.

[57] ABSTRACT

The use of an organopolysiloxane of elastomeric nature used in combination with an organic phase for the preparation of a composition and/or in a composition for removing make-up from the nails, in particular by a solvent for nail varnish. The organic phase comprises at least one organic solvent or at least one mixture of cosmetic organic solvents capable of dissolving a nail varnish and having Hansen's mean solubility parameters dD, dP and dH which satisfy the following three conditions:

(1) $dD \leq 20 \ (J/cm^3)^{1/2}$ (2) $dP \leq 10 \ (J/cm^3)^{1/2}$ (3) $dH \leq 15 \ (J/cm^3)^{1/2}$ The products for the removal of make-up from the nails, according to the invention, can give the latter, after use, a lasting soft feel without spoiling them. They are capable of not producing phenomena of drying out of the nail, nail whitening or losses in nail gloss after removal of make-up.

27 Claims, No Drawings

USE OF AN ORGANOPOLYSILOXANE OF ELASTOMERIC NATURE IN COMBINATION WITH AN ORGANIC PHASE IN A PRODUCT FOR REMOVING MAKE-UP FROM THE NAILS

The invention relates to the use of an organopolysiloxane of elastomeric nature in combination with an organic phase for the preparation of a composition and/or in a composition for removing make-up from the nails, in particular a nail varnish remover.

Nail varnish removers in thickened form, such as a cream, a gel or a paste, have been investigated for a number of years. This type of presentation is highly valued by the consumer. The formulator faces the following practical concerns: make the removal of the product from its packaging easier to control without incurring significant loss of the product; limit the spread of the product to the local region of treatment (the nail surface); and be able to employ the product in sufficient quantities to obtain the required cosmetic effect. In comparison with the conventional removers in the form of organic solutions, this thickened type of remover has been desired, since it may permit easier spreading on the nail, better-controlled dispensing of the quantity necessary for make-up removal and better effectiveness where make-up removal is concerned, by virtue of a longer contact time of the product on the nail.

Nail varnish removers of the prior art, in gel, cream or paste form, contain thickening and/or gelling agents and organic solvents capable of dissolving or decomposing the polymers like, for example, nitrocellulose, which are commonly employed for coating the nails in nail varnishes.

Published Japanese Patent Applications JP 61233607, JP 61257912, JP 02289507, JP 03074317 and JP 04164012 and U.S. Pat. No. 4,804,486, describe nail varnish removers in gel or cream form based on organic solvents such as propylene carbonate, dihydro-2-(3H)-furanone or certon and an anionic gelling agent of the type of poly(acrylic acid) polymer neutralized with alkaline substances.

Application JP 61289019 describes a remover in gel or paste form containing a hydrophilic organic solvent with a boiling point higher than 100° C., capable of dissolving nitrocellulose and a gelling agent of the sodium montmorillonite type.

Application JP 62207206 has as its subject-matter remover gels based on gamma-butyrolactone and/or benzyl alcohol and a gelling agent of the diethyl phthalate, hydroxypropylcellulose or polyvinylpyrrolidone type.

Application WO 87104921 discloses removers in gel form containing acetone as solvent, hydroxypropylcellulose as gelling agent and a nail-conditioning agent of the polyoxyethylenated fatty amine type.

After make-up removal, these compositions can result in drying out of the nail, delipidation of its surface, whitening, and losses in nail gloss. Furthermore, after application, these nail varnish removers can be less than satisfactory in imparting a lasting natural soft feel to the nail.

The inventors have surprisingly discovered that the use of at least one partially crosslinked organopolysiloxane of elastomeric nature in combination with an organic phase comprising one or several cosmetic organic solvents capable of dissolving a nail varnish and exhibiting specific solubility conditions set forth below can form a remarkable agent for removing make-up from the nails.

The inventors have discovered, in fact, that such a combination makes it possible to obtain compositions for removing make-up from the nails in gelled form which do not exhibit all the above-mentioned disadvantages and which, after removal of make-up, can unexpectedly impart to the nails a lasting soft feel and a natural gloss.

The subject-matter of the invention is the use of at least one partially crosslinked organopolysiloxane of elastomeric nature in combination with an organic phase containing at least one cosmetic organic solvent capable of dissolving a nail varnish and exhibiting Hansen's mean solubility parameters dD, dP and dH at 25° C. which satisfy the following three conditions:

(1) $dD \leq 20$ $(J/cm^3)^{1/2}$ (2) $dP \leq 10$ $(J/cm^3)^{1/2}$ and (3) $dH \leq 15$ $(J/cm^3)^{1/2}$ "Elastomeric" is intended to mean a deformable, supple material which has viscoelastic properties and preferably has the consistency of a sponge or of a supple sphere.

"Cosmetic organic solvent capable of dissolving a nail varnish" is intended to mean any cosmetically acceptable organic solvent capable of dissolving the polymer(s), the resins and/or the plasticizer(s) forming the film deposited on the nail. The said solvent must be capable in particular of dissolving nitrocellulose and the other constituents of the nail varnish.

The definition of the solvents in the three-dimensional solubility space according to Hansen is described in the paper by C. M. Hansen: "The three dimensional solubility parameters" J. Paint Technol. 39, 105 (1967), which is specifically incorporated by reference herein.

dD characterizes the London dispersion forces originating from the formation of dipoles induced during molecular impacts.

dP characterizes the Debye interaction forces between permanent dipoles and the Keesom interaction forces between induced dipoles and permanent dipoles.

dH characterizes the specific interaction forces (of the type of hydrogen bonds, acid/base, donor/ acceptor, and the like).

The parameters dD, dP and dH are expressed in $(J/cm^3)^{1/2}$.

The organopolysiloxanes of elastomeric nature in accordance with the invention are in general partially or completely crosslinked, solid and of three-dimensional structure. Included in an organic phase as defined above, they are transformed, depending on the proportion of organic phase employed, from a product of spongy appearance when they are employed in the presence of low contents of organic phase, to a homogeneous gel in the presence of larger quantities of organic phase.

The agents for removing make-up from the nails of the invention are generally in the form of gel comprising an organopolysiloxane elastomer of three-dimensional structure, included in an organic phase corresponding to the conditions specified above.

Another subject of the invention relates to cosmetic or dermatological compositions intended for removing make-up from the nails, characterized in that they contain, in a cosmetically or dermatologically acceptable medium, at least one gel phase comprising at least:

(a) at least one partially crosslinked organopolysiloxane of elastomeric nature and (b) an organic phase including at least one organic solvent ("at least one" manifestly encompasses mixtures of cosmetic organic solvents) capable of dissolving a nail varnish and exhibiting Hansen's mean solubility parameters dD, dP and dH at 25° C. which satisfy the following three conditions:

(1) dD≦20 $(J/cm^3)^{1/2}$ (2) dP≦10 $(J/cm^3)^{1/2}$ (3) dH≦15 $(J/cm^3)^{1/2}$

The organopolysiloxanes of elastomeric nature according to the invention may be chosen from the crosslinked polymers described in Application EP-A-295 886, the disclosure of which is specifically incorporated by reference herein.

According to this application, the compositions of the invention are obtained by a reaction of addition and of crosslinking of at least:

(a) an organopolysiloxane containing at least two lower alkenyl groups, such as $C_{2-6}$ alkenyl, per molecule;

(b) an organopolysiloxane containing at least two hydrogen atoms bonded to a silicon atom per molecule, wherein the organopolysiloxane (b) differs from said organopolysiloxane (a); and (c) a catalyst of the platinum type.

The organopolysiloxanes of elastomeric nature according to the invention which constitute the agent for removing make-up from the nails may be chosen from those described in documents EP-A-383540 and EP-A-545002 or U.S. Pat. No. 5,266,321, the disclosures of which are specifically incorporated by reference herein. According to this patent, they are chosen especially from:

i) the organopolysiloxanes including $R_2SiO$ and $RSiO_{1.5}$ units and optionally $R_3SiO_{0.5}$ and/or $SiO_2$ units in which the radicals R, independently of one another, denote a hydrogen, an alkyl such as methyl, ethyl or propyl, an aryl such as phenyl or tolyl, an unsaturated aliphatic group such as vinyl, and where the weight ratio of the $R_2SiO$ units to the $RSiO_{1.5}$ units varies from 1:1 to 30:1; and ii) the organopolysiloxanes which are insoluble and swellable in silicone oil, which are obtained by addition of an organohydropolysiloxane (1) and of an organopolysiloxane (2) containing unsaturated aliphatic groups in such a way that the quantity of hydrogen or of unsaturated aliphatic groups in (1) and (2) respectively ranges from 1 to 20 mol % when the organopolysiloxane is noncyclic and from 1 to 50 mol % when the organopolysiloxane is cyclic.

The organopolysiloxanes of the composition of the invention are, for example, those marketed under the names KSG6® by Shin-Etsu, Gransil® by Grant Industries (SR-CYC, SR DMF10, SR-DC556), or those marketed in the form of gels which are already made up (KSG15®, KSG17®, KSG16®, KSG18® and KSG20® by Shin-Etsu, Gransil SR 5CYC gel®, Gransil SR DMF 10 gel®, Gransil SR DC556 gel®, SF 1204® and JK 113® by General Electric). A mixture of these commercial products can also be employed.

According to the invention, when they are in powder form, before the incorporation of oils, the elastomeric organopolysiloxanes generally have a particle size of at most 1 μm, which can preferably go down to 0.5.

An organic phase permitting the swelling of the elastomeric organopolysiloxane of the invention is characterized by the fact that it contains at least one cosmetic organic solvent capable of dissolving a nail varnish and exhibiting mean solubility parameters dD, dP and dH at 25° C. according to Hansen's solubility space, which satisfy the following conditions:

(a) dD≦20 $(J/cm^3)^{1/2}$ and preferably 10≦dD≦19 $(J/cm^3)^{1/2}$ (b) dP≦10 $(J/cm^3)^{1/2}$ and preferably dP≦7 $(J/cm^3)^{1/2}$ (c) dH≦15 $(J/cm^3)^{1/2}$ and preferably dH≦13 $(J/cm^3)^{1/2}$ and more preferably dH≦8 $(J/cm^3)^{1/2}$.

The organic phase preferably includes one or several cosmetic organic solvents corresponding to the solubility conditions defined above, chosen from:

ketones, such as methyl ethyl ketone, methyl isobutyl ketone, diisobutyl ketone, isophorone, acetophenone or cyclohexanone;

alcohols, such as 1,3-dimethylbutanol, diacetone alcohol, 2-butoxyethanol or cyclohexanol;

esters, such as ethyl acetate, methyl acetate, n-butyl acetate or isoamyl acetate;

ethers, such as diethyl ether, dimethyl ether or dichlorodiethyl ether;

alkanes, such as decane, heptane, dodecane or cyclohexane;

aromatic cyclic compounds, such as toluene and styrene;

aldehydes, such as benzaldehyde or acetaldehyde.

Among these solvents for nail varnish removers those more preferably employed are esters and ketones containing at most 10 carbon atoms and more particularly methyl ethyl ketone, ethyl acetate, methyl acetate or butyl acetate.

The organic phase may also contain organic solvents for nail varnish removers which, taken as such, do not correspond to the Hansen solubility conditions defined above. This is the case with acetone, which is a very good nail varnish remover. It is also the case with some plasticizers for nitrocellulose, such as ethanol, which make it possible to soften the film deposited on the nail and to facilitate removal of make-up. In accordance with the invention, these solvents will therefore be mixed with other appropriate solvents such as those defined above, so that the overall mixture can satisfy the solubility conditions of the invention.

The organic phase is preferably present, preferably in the gel phase of the composition, in a concentration ranging from 30 to 90% by weight and more preferably from 50 to 80% by weight.

The organic phase in accordance with the invention may additionally contain an oily phase chosen so that the mixture resulting from the addition of this oily phase with the organic solvent(s) of the invention satisfies the conditions of Hansen's solubility parameters as defined above.

This oily phase may contain oils that can be directly compatible with the organopolysiloxane of elastomeric nature and that can, by themselves alone, satisfy the solubility conditions according to the invention. These oils take part in the swelling of the organopolysiloxane elastomer.

Among these swelling oils there may be mentioned:

linear or branched hydrocarbons of mineral or synthetic origin, such as liquid petrolatum, isohexadecane, isododecane, squalane and equivalents such as "parléam";

fatty alcohols such as 2-octyldodecanol;

fatty acid esters such as octyldodecyl neopentanoate;

silicone oils of low viscosity (preferably lower than 100 cSt (100 mm$^2$ s$^{-1}$) at 25° C.), such as linear or branched polysiloxanes of low degree of polymerization, like methylpolysiloxane, methylphenylpolysiloxane, ethylmethylpolysiloxane, ethylphenylpolysiloxane, hydroxymethylpolysiloxane, alkylpolydimethylsiloxane and cyclic polysiloxanes such as octamethylcyclopentasiloxane or decamethylcyclopentasiloxane, or mixtures thereof.

These particular oils are preferably employed in concentrations ranging preferably from 0 to 50% by weight and more preferably from 0 to 40% by weight relative to the total weight of the mixture formed by the organopolysiloxane of elastomeric nature and the said swelling oils.

The additional oily phase may contain polar oils such as mineral or synthetic oils, for example hydrogenated polyisobutenes, vegetable oils like liquid triglycerides, for example sunflower, corn, soya, gourd, grapeseed, sesame, hazelnut, apricot, macadamia or castor oils, triglycerides of caprylic/capric acids like those sold by the company Stearineries Dubois or those sold under the names Miglyol 810, 812 and 818 by Dynamit Nobel. These polar oils preferably represent from 0 to 30% by weight relative to the total weight of the oily phase.

The additional oily phase is present, preferably in the gel phase, in concentrations ranging preferably from 0 to 65% by weight and more preferably from 0 to 50% by weight relative to the total weight of the gel phase.

The elastomeric organopolysiloxane is present, preferably in the gel phase, in a concentration of active substance preferably ranging from 5 to 70% by weight and more preferably from 20 to 50% by weight.

The composition resulting from this combined use, preferably in gel form, may be employed as it is and may itself form a composition for the removal of make-up from the nails. It can also be incorporated into a nail varnish remover formulation in an effective quantity to obtain both the texture and the viscosity which are desired and good removal of make-up from the nails.

The compositions according to the invention containing the agents for removing make-up as defined above are preferably in the form of gels which can be translucent or opaque.

They may additionally contain traditional adjuvants such as dyes, perfumes, preserving agents, sunscreens or hydrating agents. These adjuvants are present in quantities ranging preferably from 0 to 20% by weight relative to the weight of the composition.

The invention also relates to a process for removing make-up from the nails, characterized by the fact that an effective quantity of a composition containing an organopolysiloxane elastomer as defined above and an organic phase as defined above, preferably a composition containing a gel formed from an organopolysiloxane elastomer as defined above and from an organic phase as defined above, is applied to the surface of the nail.

The examples which follow are used to illustrate the invention without, however, being limiting in character.

EXAMPLE 1

Nail Varnish Remover Gel

| | |
|---|---|
| Mixture of 40% by weight polydimethylsiloxane 6 cSt (6 mm² s⁻¹) oil and of 60% by weight of partially crosslinked polydimethylorganosiloxane sold under the name KSG 6 ® by Shin Etsu | 30% by weight |
| Ethyl acetate | 50% by weight |
| Hydrogenated isoparaffin (Parleam) | 9.5% by weight |
| Perfume | 0.5% by weight |
| Dye | 0.0005% by weight |
| Polydimethylsiloxane sold under the name Dow Corning 200-Fluid ® by Dow Corning    q.s. | 100% by weight |

A gel is obtained which is easy to spread and which, after removal of make-up and cleaning with a swab, imparts a lasting natural soft feel to the nails. The nails from which make-up has been removed have a natural appearance. They remain glossy and are not whitened.

EXAMPLE 2

Nail Varnish Remover Gel

| | |
|---|---|
| Mixture of 40% by weight polydimethylsiloxane 6 cSt (6 mm² s⁻¹) oil and of 60% by weight of partially crosslinked polydimethylorganosiloxane sold under the name KSG 6 ® by Shin Etsu | 30% by weight |
| Methyl ethyl ketone | |
| Diethyl ether | |
| Methyl acetate | 45.6% by weight |
| Perfume | 1% by weight |
| Dye | 0.0005% by weight |
| Triglycerides of caprylic/capric acids sold under the name Miglyol ® by Dynamit Nobel   q.s. | 100% by weight |

A gel is obtained which is easy to spread and which, after removal of make-up and cleaning with a swab, imparts a lasting natural soft feel to the nails. The nails from which make-up has been removed have a natural appearance. They remain glossy and are not whitened.

EXAMPLE 3

Nail Varnish Remover Gel

| | |
|---|---|
| Partially crosslinked dimethylpolysiloxane sold under the name Trefil E505C ® by Dow Corning-Toray Silicone | 25% by weight |
| Ethyl acetate | 58% by weight |
| Acetone | 8% by weight |
| Glycerine | 3% by weight |
| Perfume | 1% by weight |
| Dye | 0.0005% by weight |
| Hydrogenated polyisobutene   q.s. | 100% by weight |

A gel is obtained which is easy to spread and which, after removal of make-up and cleaning with a swab, imparts a lasting natural soft feel to the nails. The nails from which make-up has been removed have a natural appearance. They remain glossy and are not whitened.

We claim:

1. A process for the preparation of a composition for removing make-up from the nails comprising the step of including in said composition at least one partially crosslinked organopolysiloxane of elastomeric nature and an organic phase comprising at least one cosmetic organic solvent for dissolving nail varnish, said cosmetic organic solvent exhibiting Hansen's mean solubility parameters dD, dP and dH at 25° C. which satisfy the following three conditions:

(1) $dD \leq 20$ $(J/cm^3)^{1/2}$ (2) $dP \leq 10$ $(J/cm^3)^{1/2}$ and (3) $dH \leq 15$ $(J/cm^3)^{1/2}$.

2. A process according to claim 1 wherein said at least one organopolysiloxane is included in the organic phase to form a gel.

3. A process according to claim 1 wherein said at least one organopolysiloxane is completely crosslinked.

4. A process according to claim 1 wherein said composition is a nail varnish remover in gel form.

5. A process according to claim 1 wherein said at least one organopolysiloxane is obtained by the addition and crosslinking of:

(a) at least one organopolysiloxane containing at least two lower alkenyl groups per molecule;

(b) at least one organopolysiloxane containing at least two hydrogen atoms bonded to a silicon atom per molecule, wherein said at least one organopolysiloxane (b) differs from said at least one organopolysiloxane (a); and (c) at least one platinum catalyst.

6. A process according to claim 1 wherein said at least one organopolysiloxane is selected from:

i) organopolysiloxanes containing $R_2SiO$ and $RSiO_{1.5}$ units and optionally $R_3SiO_{0.5}$ and/or $SiO_2$ units wherein the said radicals R, $R_2$ and $R_3$, independently of one another, denote a hydrogen, an alkyl, an aryl, or an unsaturated aliphatic group, and further wherein the weight ratio of the $R_2SiO$ units to the $RSiO_{1.5}$ units ranges from 1:1 to 30:1;

ii) organopolysiloxanes which are insoluble and swellable in silicone oil, said organopolysiloxanes being obtained by addition of an organohydropolysiloxane to an organopolysiloxane containing unsaturated aliphatic groups, the quantity of hydrogen or of unsaturated aliphatic groups in said organohydropolysiloxane and said organopolysiloxane respectively ranging from 1 to 20 mol % when the organopolysiloxane is noncyclic and from 1 to 50 mol % when the organopolysiloxane is cyclic.

7. A process according to claim 6 wherein said alkyl group is selected from methyl, ethyl and propyl.

8. A process according to claim 6 wherein said aryl group is selected from phenyl and tolyl.

9. A process according to claim 6 wherein said unsaturated aliphatic group is vinyl.

10. A process according to claim 1 wherein said at least one cosmetic organic solvent for dissolving nail varnish exhibits Hansen's mean solubility parameters dD, dP and dH at 25° C. corresponding to the following three conditions:

(a) $10 \leq dD \leq 19$ $(J/cm^3)^{1/2}$ (b) $dP \leq 7$ $(J/cm^3)^{1/2}$ and (c) $dH \leq 13$ $(J/cm^3)^{1/2}$.

11. A process according to claim 1 wherein said at least one cosmetic organic solvent is selected from:
ketones,
alcohols,
esters,
ethers,
alkanes,
aromatic cyclic compounds, and
aldehydes.

12. A process according to claim 11 wherein said at least one cosmetic organic solvent is selected from esters and ketones containing at most 10 carbon atoms.

13. A process according to claim 1 wherein said organic phase further comprises an oily phase selected such that the mixture resulting from the addition of this oily phase to said organic phase satisfies the conditions of Hansen's solubility parameters as defined in claim 1.

14. A process according to claim 13 wherein said oily phase comprises at least one oil selected from:
alkanes,
fatty alcohols,
acid esters, and
silicone oils of low viscosity.

15. A process according to claim 14 wherein said silicone oils have a viscosity lower than 100 cSt (100 mm$^2$ s$^{-1}$) at 25° C.

16. A process according to claim 14 wherein said silicone oils are selected from linear and branched polysiloxanes of low degree of polymerization and cyclic polysiloxanes.

17. A process according to claim 13 wherein said oily phase comprises at least one polar oil.

18. A process according to claim 17 wherein said at least one polar oil represents from up to 30% by weight relative to the total weight of the oily phase.

19. A process according to claim 13 wherein said composition contains a gel phase and wherein said oily phase is present in said gel phase of the composition in a concentration ranging up to 65% by weight relative to the total weight of the gel phase.

20. A process according to claim 19 wherein said concentration ranges up to 50% by weight relative to the total weight of the gel phase.

21. A process according to claim 2 wherein said organic phase is present in the gel phase of the composition in a concentration ranging from 30 to 90% by weight relative to the total weight of the gel phase.

22. A process according to claim 21 wherein said concentration ranges from 50 to 80% by weight relative to the total weight of the gel phase.

23. A process according to claim 2 wherein said at least one organopolysiloxane is present in the gel phase in a concentration of active substance ranging from 5 to 70% by weight.

24. A process according to claim 23 wherein said concentration ranges from 20 to 50% by weight.

25. A cosmetic or dermatological composition intended for removing make-up from the nails, comprising at least one gel phase comprised of (a) at least one partially crosslinked organopolysiloxane of elastomeric nature and (b) an organic phase as defined in claim 1.

26. A composition according to claim 25 wherein said composition further comprises a cosmetically or dermatologically acceptable medium.

27. A composition according to claim 25 wherein said composition is a nail varnish remover in gel form.

* * * * *